US012059682B2

(12) United States Patent
Jung et al.

(10) Patent No.: US 12,059,682 B2
(45) Date of Patent: Aug. 13, 2024

(54) METHOD FOR ISOLATION AND MORPHOLOGICAL ANALYSIS OF CELLS

(71) Applicants: EzDiaTech Inc., Cheonan-si (KR); University-Industry Cooperation Group of Kyung Hee University, Yongin-si (KR)

(72) Inventors: Yong Gyun Jung, Seoul (KR); Joo Ho Kim, Yongin-si (KR); Wook Park, Suwon-si (KR); Jin Sik Yoon, Suwon-si (KR); Suk Heung Song, Yongin-si (KR)

(73) Assignees: EZDIATECH INC., Cheonan-si (KR); UNIVERSITY—INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 1316 days.

(21) Appl. No.: 16/166,209

(22) Filed: Oct. 22, 2018

(65) Prior Publication Data
US 2020/0122137 A1    Apr. 23, 2020

(51) Int. Cl.
*B01L 3/00* (2006.01)
*C12M 1/32* (2006.01)

(52) U.S. Cl.
CPC .......... *B01L 3/5085* (2013.01); *B01L 3/5027* (2013.01); *C12M 23/12* (2013.01); *B01L 2300/069* (2013.01); *B01L 2300/0829* (2013.01); *B01L 2300/0851* (2013.01); *B01L 2300/16* (2013.01)

(58) Field of Classification Search
CPC ................. C12M 47/04; B01L 2300/0829
USPC .................................. 422/552, 603
See application file for complete search history.

(56) References Cited

U.S. PATENT DOCUMENTS

| 9,133,498 B2 | 9/2015 | Kwon et al. | |
| 9,920,351 B2 | 3/2018 | Kwon et al. | |
| 2003/0040033 A1* | 2/2003 | Kim | B82Y 30/00 435/32 |
| 2007/0292837 A1* | 12/2007 | Deutsch | B29C 65/002 435/174 |

OTHER PUBLICATIONS

Gopakumar Kamalakshakurup et al.; High-efficiency single cell encapsulation and size selective capture of cells in bicoliter droplets based on hydrodynamic micro-vortices; Lab on a Chip; 2017, vol. 17, p. 4324; The Royal Society of Chemistry; UK.

(Continued)

*Primary Examiner* — Natalia Levkovich
(74) *Attorney, Agent, or Firm* — STIP Law Group, LLC

(57) ABSTRACT

Provided is a method for cell isolation and morphological analysis. The method includes: providing a substrate with one or more wells; inserting cell isolation devices, each of which has one side patterned with one or more microwells, into the wells; introducing a liquid medium including cells into the wells; allowing the microwells of the cell isolation devices to come into contact with the inner surfaces of the wells such that some of the cells are isolated and trapped at the level of individual cells in the microwells; and observing the morphological changes of the isolated cells.

5 Claims, 10 Drawing Sheets

(56) References Cited

OTHER PUBLICATIONS

Jungil Choi et al.; Rapid antibiotic susceptibility testing by tracking single cell growth in a microfluidic agarose channel system; Lab on a Chip; 2013, vol. 13, p. 280; The Royal Society of Chemistry; UK.
Yi Lu et al.; Single Cell Antimicrobial Susceptibility Testing by Confined Microchannels and Electrokinetic Loading; Analytical Chemistry; 2013, vol. 85, pp. 3971-3976; ACS; USA.

* cited by examiner

Fig. 5
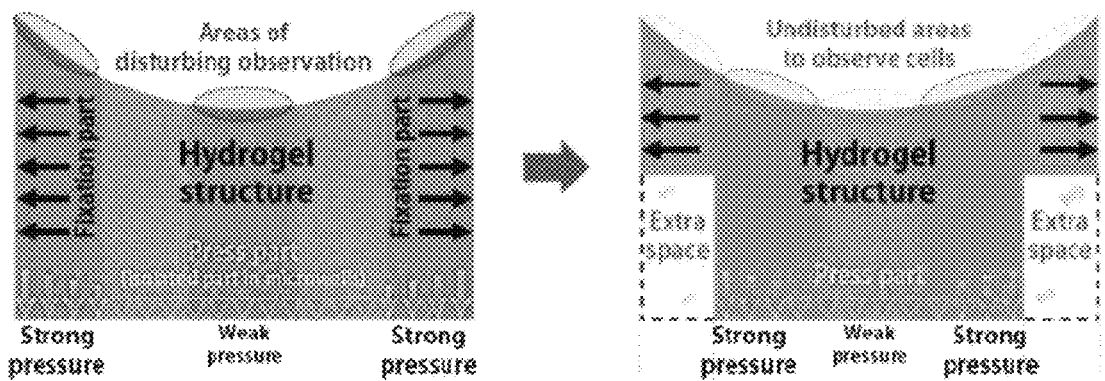
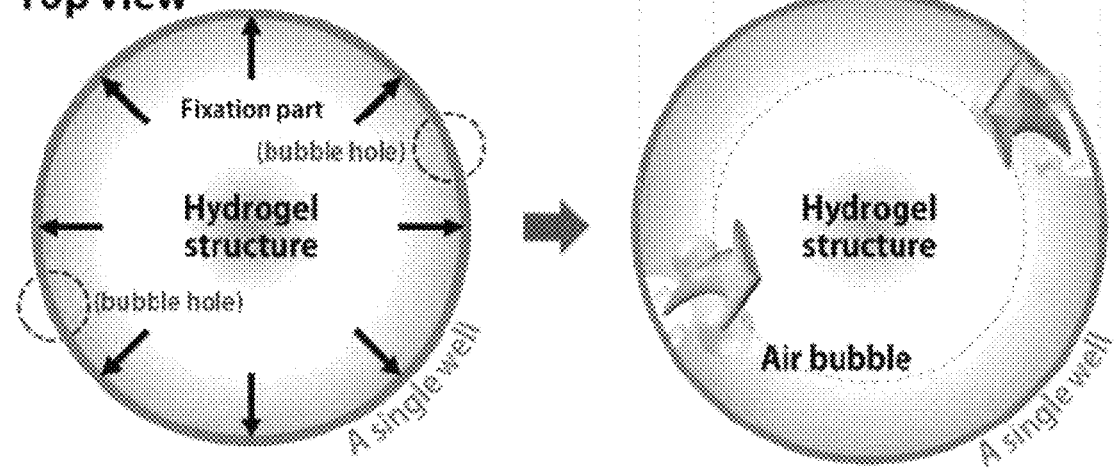

METHOD FOR ISOLATION AND MORPHOLOGICAL ANALYSIS OF CELLS

BACKGROUND OF THE INVENTION

1. Field of the Invention

The present disclosure relates to a method for cell isolation and morphological analysis, and more specifically to a method, device, and kit for dissociating cell colonies into single cells and effectively analyzing the morphological changes of the cells.

2. Description of the Related Art

Cell immobilization is essential for effective observation of cell growth changes, morphology or migration. Particularly, cell immobilization techniques are used to immobilize floating cells on a single cell basis and effectively observe the morphology changes and migration of the cells over time. In attempts to immobilize cells for observation, many methods have been developed so far, for example, methods for immobilizing cells with cell-sized microfluidic structures into which the cells are allowed to flow, methods for immobilizing cells with microfluidic structures wherein an air pressure is used to arbitrarily make the intervals between the microfluidic structures narrow, and methods for immobilizing cells in a hydrogel matrix by mixing a hydrogel including agarose with the cells. However, the use of the microfluidic structures requires a precise and expensive pump system that forces cells to flow into the microfluidic structures and supplies an air pressure to the microfluidic structures. Further, the complicated procedure greatly limits the morphological analysis of cells. The cell immobilization in the hydrogel matrix is not suitable for various morphological analyses of cells because cells tend to aggregate and grow. Further, these conventional cell immobilization methods have many difficulties in achieving high throughput. Thus, there is a need to provide an improved morphological/intracellular metabolic analysis method that overcomes the problems encountered in the conventional cell immobilization techniques, including 1) need for an extra system, 2) high cost, 3) complicated procedure, and 4) limited throughput.

On the other hand, an antibiotic susceptibility test is a useful tool that can be applied to methods for cell immobilization and morphological analysis. Sepsis is a critical life-threatening condition from bacterial infection and sends numerous patients to the intensive care unit of the hospital only to die every year. Owing to the dramatically increasing rate of sepsis mortality, proper treatment with rapid diagnosis is important. The antibiotic susceptibility test (AST) is a clinical method to detect resistance or susceptibility of pathogens against antibiotics for treatment. However, the conventional AST methods used in ordinary practice consume a lot of time (18-24 hours) and cannot respond to sepsis efficiently. Because of the long lead-time, the initial antibiotic treatment is based on the physician's discretion, thus the possibility of antibiotic misuse and overuse has remained. If a valuable AST system can detect antibiotic resistance or susceptibility correctly in just a few hours, patient mortality due to sepsis and misdiagnosis can be reduced considerably in the clinical arena.

Although numerous AST approaches have been studied, molecular and cell culturing systems are typical. The molecular AST method can obtain results quickly, in just a few hours, but can be adopted only in restrictive conditions with analytical equipment such as PCR machine and requires much more research to be used widely in clinical applications. In contrast with the molecular method, the cell culturing system is accurate and most used in the clinical arena, so it is regarded as the standard AST system. The most commonly employed AST process in the cell culturing system is the liquid microdilution method. This traditional AST system requires 18~24 hours because the liquid microdilution method determines the minimum inhibitory concentration (MIC) of the relevant antibiotics by identifying a change in turbidity of culture wells. The turbidity is indirectly measured by optical density (OD) coming from cell growth, which is proportional to the concentration of the bacterial cells in the culture well. However, the OD evaluation is not sensitive to the bacterial cell population expansion when the concentration of the bacterial cells is conspicuously low. Thus, it needs 18-24 hours to accurately distinguish whether the bacterial cells grow or not under particular concentrations of antibiotics.

To overcome the limitations of the traditional AST system, a number of researchers have developed a variety of methods for rapid detection of early-stage bacterial growth. Previous researchers developed numerous methods such as using fluidic channels or droplets emitting chemical signals to detect the bacterial cell growth. These systems allow for the inspection of the bacterial variations at an early stage, but they require supplementary apparatus and intricate processes. In addition, theoretically, the fastest method for detection of bacterial cell growth is to monitor single bacterial cells, but they cannot detect the division of individual bacterial cells. Therefore, researchers need to isolate bacterial cells from culture to observe them under a microscope and then analyze the morphological changes of the individual cells. Bacterial cell immobilization plays a decisive role in the inspection of single cell morphology because most bacterial cells are mobile in culture medium. Outstanding prior research has been conducted so far, although these methods also require additional processes and cumbersome and pricey equipment for bacterial immobilization, for instance, by employing microchannel systems to monitor single cell morphology under an antibiotic environment.

SUMMARY OF THE INVENTION

According to one aspect of the present disclosure, there is provided a method for cell isolation and morphological analysis including: providing a substrate with one or more wells; inserting cell isolation devices, each of which has one side patterned with one or more microwells, into the wells; introducing a liquid medium including cells into the wells; allowing the microwells of the cell isolation devices to come into contact with the inner surfaces of the wells such that some of the cells are isolated and trapped at the level of individual cells in the microwells; and observing the morphological changes of the isolated cells.

According to a further aspect of the present disclosure, there is provided a method for cell isolation and morphological analysis including: providing a substrate with one or more wells; inserting cell isolation devices, each of which has one side patterned with one or more microwells, into the wells; introducing a liquid medium including microbial cells and bioactive agents into the wells; allowing the microwells of the cell isolation devices to come into contact with the inner surfaces of the wells such that some of the microbial cells are isolated and trapped at the level of individual cells in the microwells; and observing the morphological/metabolic changes of the isolated cells according to the kind of the bioactive agents over time to determine cytotoxicity, cell proliferation/survival/apoptosis or changes in the amount of metabolites in the cells.

According to a further aspect of the present disclosure, there is provided a method for cell isolation and morphological analysis including: providing a substrate with one or more wells; inserting cell isolation devices, each of which has one side patterned with one or more microwells, into the wells; introducing a liquid medium including microbial cells, nutrients, and antibiotics into the wells; allowing the microwells of the cell isolation devices to come into contact with the inner surfaces of the wells such that some of the microbial cells are isolated and trapped at the level of individual cells in the microwells; and observing the morphological changes of the isolated microbial cells over time to determine minimum inhibitory concentration (MIC).

According to a further aspect of the present disclosure, there is provided a cell isolation device for cell analysis including: a body made of a swellable material whose volume varies in response to an external stimulus and one or more microwells patterned at least one side of the body wherein the cell isolation device has a size small enough to be inserted into a well of a substrate and the entrance of each microwell comes into close contact with at least one inner surface of the corresponding well when the swellable material swells by an externally applied stimulus so that cells are isolated and trapped at the level of individual cells in the microwell.

According to another aspect of the present disclosure, there is provided a kit for cell isolation and morphological analysis including a substrate with one or more wells and the cell isolation device inserted and arranged in each well of the substrate.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 5 compares the structures of two cell isolation devices including bottom portions having different diameters;

DETAILED DESCRIPTION OF THE INVENTION

Figure 1:
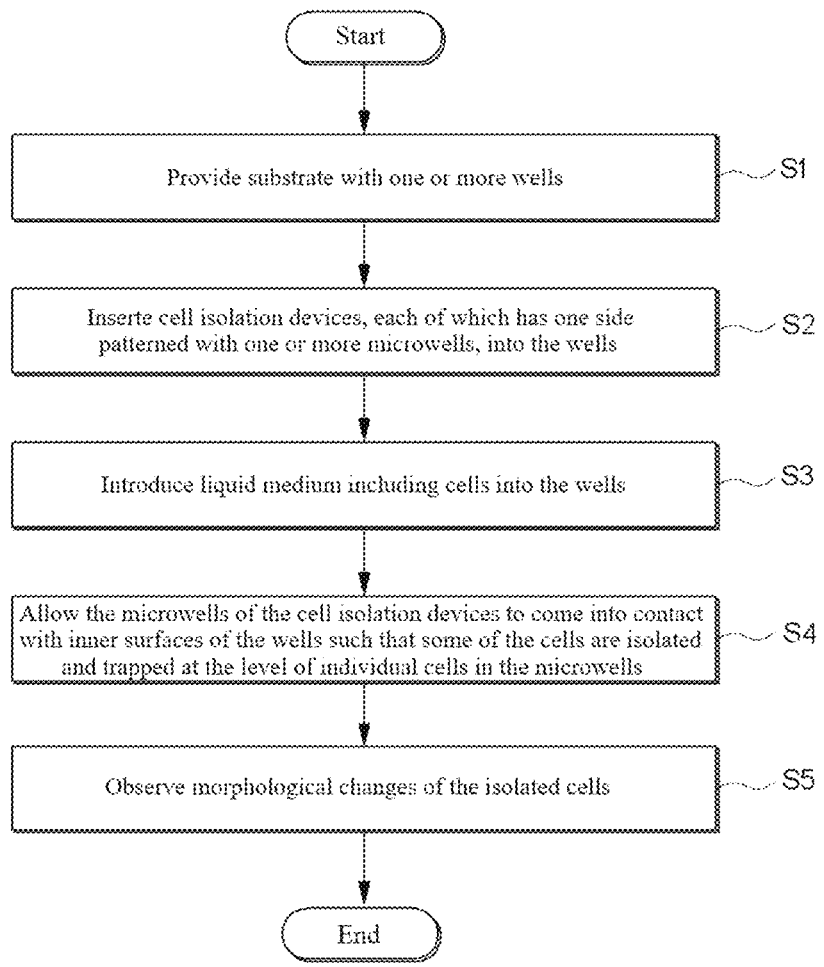
FIG. 1 is a flowchart illustrating one embodiment of a method for cell isolation and morphological analysis.

As used herein, the singular forms "a", "an" and "the" are intended to include the plural forms as well, unless the context clearly indicates otherwise. As used herein, the term "or" means "and/or" unless otherwise mentioned. Furthermore, the terms "including" and other forms, for example, "having", "consisting of", and "composed of" are not limited.

As used herein, the term "cells" is intended to include animal cells, plant cells, and microbial cells.

As used herein, the term "microbe" is intended to include all gram-negative (−) bacteria, gram-positive (+) bacteria, fungi, and Archimycetes, but is not limited thereto. Specifically, the microbe can be selected from the group consisting of, but not limited to, *Enterococcus, Streptococcus, Pseudomonas, Salmonella, Escherichia coli, Staphylococcus, Lactococcus, Lactobacillus, Enterobacteriaceae, Klebsiella, Providencia, Proteus, Morganella, Acinetobacter, Burkholderia, Stenotrophomonas, Alcaligenes,* and *Mycobacterium*. More specific examples of such microbes include, but are not limited to, *Enterococcus faecium, Staphylococcus aureus, Klebsiella species, Acinetobacter baumannii, Pseudomonas aeruginosa,* and *Enterobacter* species.

As used herein, the term "bioactive agent" may include a substance selected from antibiotics, anticancer agents, and drugs such as immunosuppressants, nutrients, cellular secretions, signal transducers, viruses, cells, micro RNAs, proteins, antigens, antibodies, and DNA.

As used herein, the term "antibiotic" is selected from the group consisting of, but not limited to, amikacin, amoxicillin, ampicillin, aztreonam, benzylpenicillin, clavulanic acid, cefazolin, cefepime, cefotaxime, cefotetan, cefoxitin, cefpodoxime, ceftazidime, ceftriaxone, cefuroxime, ciprofloxacin, dalfopristin, doripenem, daptomycin, ertapenem, erythromycin, gentamicin, imipenem, levofloxacin, linezolid, meropenem, minocycline, moxifloxacin, nitrofurantoin, norfloxacin, piperacillin, quinupristin, rifampicin, streptomycin, sulbactam, sulfamethoxazole, telithromycin, tetracycline, ticarcillin, tigecycline, tobramycin, trimethoprim, vancomycin, and mixtures thereof.

As used herein, the term "changes in the growth of cells" refers to the responses of cells to the bioactive agent and can be classified into dividing, no-change, filament formation, and swelling formation.

The term "morphological changes of cells" can be interchangeably used with the term "changes in the growth and migration of cells".

The term "dividing" means that a microbial cell is divided into two cells under non-antibiotic and antibiotic resistant conditions, and consequently, that not only the number of microbial cells but also an OD value of BMD experiment are increased.

The term "no-change" means that a microbial cell is susceptible to the bioactive agent and does not grow.

The term "filament formation" means that a cell does not divide but grows lengthwise. The filament formation may include the responses of the microbe to β-lactam antimicrobial agents. Specifically, the filament formation may include the responses of the microbe except for the responses of gram-negative bacteria to penems as β-lactam antibiotics.

More specifically, the filament formation may include the responses of the microbe except for the responses of *Pseudomonas aeruginosa* or *Escherichia coli* to penems as β-lactam antibiotics.

The term "swelling formation" means that a cell does not divide but swells and grows. The swelling formation may include the responses of the microbe to penems as β-lactam antibiotics. Specifically, the swelling formation may include the responses of gram-negative bacteria to imipenem or meropenem. More specifically, the swelling formation may include the responses of *Pseudomonas aeruginosa* and *Escherichia coli* to imipenem or meropenem.

The present disclosure will now be described in more detail with reference to the accompanying drawings.

One aspect of the present disclosure provides a method for cell isolation and morphological analysis. FIG. 1 is a flowchart illustrating one embodiment of a method for cell isolation and morphological analysis. Referring to FIG. 1, in S1, a substrate with one or more wells is provided.

The substrate may be a commercially available multi-well plate. Multi-well plates are standard tools for treating and analyzing a large number of samples in chemical, biochemical and/or biological assays. Multi-well plates may take various forms, sizes and shapes. Generally, multi-well plates are produced to have standard sizes and shapes and have standard arrangements of wells. The standard arrangements of wells include those found in 6-well plates (3×2 array of wells), 12-well plates (4×3 array of wells), 24-well plates (6×4 array of wells), 96-well plates (12×8 array of wells), 384-well plates (24×16 array of wells), and 1536-well plates (48×32 array of wells). Multi-well plates having other arrangements of wells are commercially available. The method of the present disclosure using a commercial multi-well plate is readily compatible with various conventional biological analysis techniques.

In S2, cell isolation devices, each of which has one side patterned with one or more microwells, are inserted into the wells. The microwells are designed to isolate and trap cells at the level of individual cells. The number and dimensions of the microwells can be determined depending on the kind and analytical purpose of an analyte sample. For example, 1 to 1,000,000 microwells may be assigned to each well of the substrate. The microwells may have a diameter of 2 to 900 μm and a depth of 2 to 900 μm. The shape of the microwells is not particularly limited and may vary depending on the intended purpose. For example, the microwells may have a circular, elliptical or polygonal shape in cross section.

The cell isolation devices may include a swellable material whose volume varies in response to an external stimulus. For cost reduction and ease of fabrication, almost all portions of the body of each of the cell isolation devices are made of a swellable material.

A hydrogel is preferably used as the swellable material due to its biocompatibility and ability to swell. Any energy or external substance that can induce a change in the volume of the swellable material when applied to the swellable material may be used without particular limitation as the external stimulus. The external stimulus can be selected from the group consisting of light, sound, heat, electricity, magnetism, specific substances, and combinations thereof. Here, the specific substances may be gaseous, liquid, and solid substances, for example, water, organic solvents, acids, and bases. When the swellable material is a hydrogel, the external stimulus is preferably water. The water may be supplied from a cell culture medium.

The hydrogel refers to a substance formed when an organic polymer (natural or synthetic) is cross-linked via covalent, ionic, or hydrogen bonds to create a three-dimensional open-lattice structure which entraps water molecules to form a gel. The hydrogel refers to a polymer that is non-toxic to cells and that forms a gel that allows for sufficient diffusion of oxygen and nutrients to maintain viability to the captured cells. The hydrogel may be made of a natural or synthetic material. Examples of suitable materials for the hydrogel include polysaccharides such as alginate, collagen, chitosan, sodium cellulose sulfate, gelatin and agarose, water soluble polyacrylates, poly(phosphazines), poly(acrylic acids), poly(methacrylic acids), poly(alkylene oxides), poly(vinyl acetate), polyvinylpyrrolidone (PVP), and copolymers and blends of each. The hydrogel may be prepared by photocuring a corresponding monomer as a raw material. For example, a water soluble polyacrylate hydrogel may be prepared by photocuring poly(ethylene glycol) diacrylate in water in the presence of an initiator.

In S3, a liquid medium including cells is introduced into the wells. The liquid medium may further include nutrients or bioactive agents such as antibiotics.

The cells may be present at a concentration of 1 to $10^{10}$ CFU/mL in the liquid medium.

In S4, the microwells of the cell isolation devices are allowed to come into contact with the inner surfaces of the wells such that some of the cells are isolated and trapped at the level of individual cells in the microwells.

When the microwells come into contact with the inner surfaces (for example, bottom surfaces) of the wells, the floating cells are trapped in the narrow spaces of the microwells. This trapping is effective in immobilizing the cells without substantially floating, making it easy to observe cell morphological changes over time. The microwells can be brought into contact with the inner surfaces of the wells by various means. For example, the patterned surfaces of the microwells can be brought into close contact with the inner surfaces of the wells by an increase in the volume of the swellable material in response to the external stimulus. The volume of the swellable material can be increased to 1.01 to 50 times its initial volume.

As used herein, the term "level of individual cells" means the level at which the morphological changes of cells can be measured without being disturbed. The level of individual cells means the presence of 1 to 1,000, preferably 1 to 10 cells, in an isolated space between the microwell and the well when ease of tracking the morphological change is taken into consideration. Preferably, the concentration of the cells is controlled such that the cells are isolated at the level of individual cells.

The cells isolated at the level of individual cells may be distributed two-dimensionally on the bottom of the wells. The method of the present disclosure facilitates focusing on the cells upon microscopic observation compared to three-dimensional immobilization approaches using agarose (for example, see U.S. Pat. Nos. 9,133,498 and 9,920,351).

The number of the cells isolated in each microwell can be determined and controlled depending on various factors such as the concentration of the cells in the liquid medium, the number and dimensions of the microwell patterns, and the design of the cell isolation devices. The isolation of the cells at the level of individual cells from cell colonies facilitates observation of the same or different types of single cells in each microwell.

In S5, the morphological changes of the isolated cells are observed. At least a portion of the body of each cell isolation device may be made of an optically transparent material through which light from an external light source can be transmitted such that the analytes in the microwells are observable.

An optical measurement system may be used for observation. The optical measurement system may include an imaging system, such as a CCD or CMOS camera. The optical measurement system may include optical units or devices necessary for focusing and light imaging, such as a lens, an illuminator, and a light guide. The optical measurement system may include an image processing system for processing and analyzing image data observed by the imaging system. The optical measurement system rapidly records and analyzes the morphological changes of the cells observed during testing to obtain test results.

A further aspect of the present disclosure provides a method for cell isolation and morphological analysis including observing the morphological/metabolic changes of the isolated cells according to the kind of the bioactive agents over time to determine cytotoxicity, cell proliferation/survival/apoptosis or changes in the amount of metabolites in the cells. Specifically, after the cell isolation devices are inserted into the wells of the substrate, a liquid medium including microbial cells and bioactive agents is introduced into the wells. Next, some of the microbial cells are isolated and trapped at the level of individual cells in the microwells. Thereafter, the morphological/metabolic changes of the isolated cells are observed according to the kind of the bioactive agents over time to inspect cell responses. At this time, a reagent such as a cell staining reagent can be used to assist in observing the isolated cells.

Another aspect of the present disclosure provides a method for cell isolation and morphological analysis including observing the morphological changes of the isolated microbial cells over time to determine minimum inhibitory concentration (MIC). Specifically, after the cell isolation devices are inserted into the wells of the substrate, a liquid medium including microbial cells, nutrients, and antibiotics is introduced into the wells. Next, some of the microbial cells are isolated and trapped at the level of individual cells in the microwells. Thereafter, the morphological changes of the isolated cells are observed over time to determine the minimum inhibitory concentration (MIC) values of the antibiotics.

The observation of the morphological changes may include observing the individual responses of the single microbial cells to the antibiotics, observing whether the microbial cells form colonies or observing the colony forming units (CFU).

The method may further include imaging the individual responses of the single microbial cells to the antibiotics, the colonies of the microbial cells or the colony forming units (CFU), and analyzing the images.

An antibiotic susceptibility test is based on the analysis of the morphological changes of microbial cells in response to antibiotics by time-lapse imaging. Specifically, the microbial cells are determined to be resistant to the antibiotics when they are observed to divide and to be susceptible when no-change, filament formation and swelling formation of the microbial cells are observed.

Figure 2:
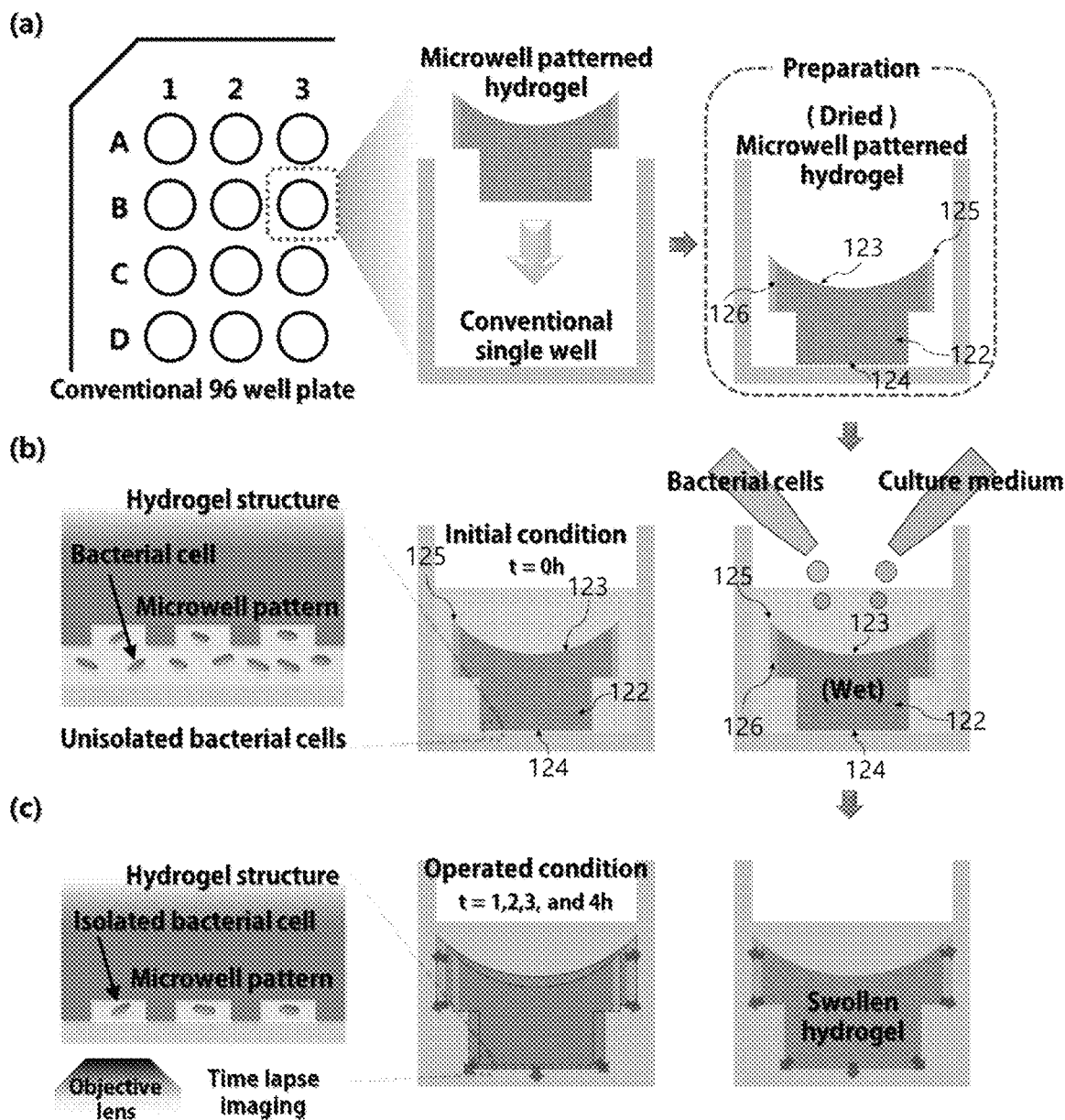
FIG. 2 is a schematic diagram illustrating a technique for dissociating cell colonies into cells at the level of individual cells and continuously observing the morphological changes of the isolated single cells by utilizing a hydrogel structure according to one embodiment of the present disclosure.

FIG. 2 is a schematic diagram illustrating a technique for dissociating cell colonies into cells at the level of individual cells and continuously observing the morphological changes of the isolated single cells by utilizing a hydrogel structure according to one embodiment of the present disclosure. Referring to (a) of FIG. 2, a conventional 96 well plate is prepared, and thereafter, a dried microwell-patterned hydrogel is inserted into each well. Referring next to (b) of FIG. 2, a cell culture medium containing bacterial cells, nutrients and antibiotics is introduced into each well containing the dry microwell-patterned hydrogel. At the initial stage of introduction, the bottom microwells of the microwell-patterned hydrogel are not yet seated on the base of the well and the microwell-patterned hydrogel is slightly floating. Thus, the bacterial cells are free to move in and out of each microwell pattern.

Referring to (c) of FIG. 2, several or tens of minutes after the introduction, the microwell-patterned hydrogel swells and approaches the inner wall of the well. As a result, the top of the microwell-patterned hydrogel is in close contact with the inner sidewall of the well and the bottom of the microwell-patterned hydrogel is seated on and remains attached to the base of the well. At this time, the individual bacterial cell entering the space of each bottom microwell pattern of the microwell-patterned hydrogel is not free to move any further in and out of the microwell pattern and is isolated in the microwell-patterned area due to the pressure of the swollen hydrogel. In a state in which the hydrogel is fully expanded, continuous bacterial morphological changes can be observed after several hours by time-lapse imaging through an objective lens of the optical measurement system. As a result, time-lapse images of the individual bacterial cells can be obtained.

Figure 3:
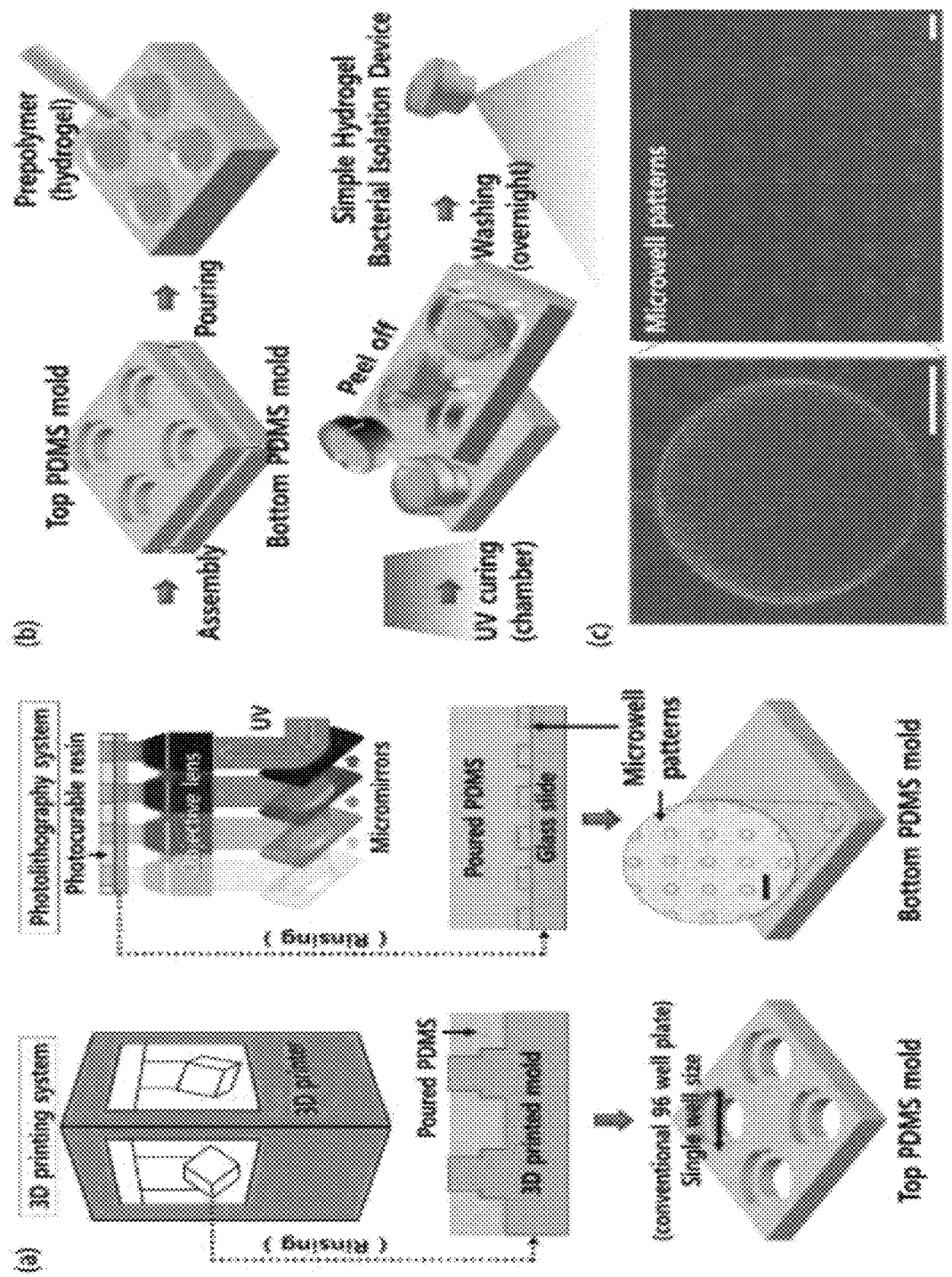
FIG. 3 shows a fabrication process of a simple hydrogel bacterial isolation device.

For example, the microwell-patterned hydrogel structure may be designed and fabricated by the following procedure. FIG. 3 shows a fabrication process of a simple hydrogel bacterial isolation device. Referring to (a) of FIG. 3, first, top and bottom polydimethylsiloxane (PDMS) molds are fabricated. To this end, top and bottom master molds are created using a three-dimensional printer and photolithography system. The PDMS material is poured onto the two mold substrates and baked to obtain the assembled top and bottom PDMS mold. The circular image surrounded by a dashed line shows an enlargement of the bottom PDMS mold surface from an optical microscope (scale bar: 100 μm).

The top master mold is produced from the 3D printing system with the desired dimensions for each well of a conventional 96 well plate, and the bottom master mold is fabricated using the photolithography system, using prepolymers (polyurethane acrylate, PUA 311), and 3-(trimethoxysilyl)propyl methacrylate on coated glass slides. Then, the precise amounts of PDMS prepolymers and a photoinitiator are poured on the top and bottom master molds, photocured, and further cured at room temperature overnight.

Referring to (b) of FIG. 3, after assembling the top and bottom PDMS molds produced, the poly(ethylene glycol) diacrylate hydrogel prepolymer is poured into the space of the assembled top and bottom PDMS mold and the simple hydrogel bacterial isolation devices are fabricated by photocuring for 15 minutes in a UV chamber. The new hydrogel structure is peeled from the mold assembly, washed with 99% ethanol, and dried at room temperature overnight.

The microwell patterns of the hydrogel structure are observed and confirmed by scanning electron microscope (SEM) as shown in (c) of FIG. 3. The right image shows the microwell patterns (scale bar: 50 μm) and the left image shows an enlarged single microwell (scale bar: 10 μm).

Figure 4:
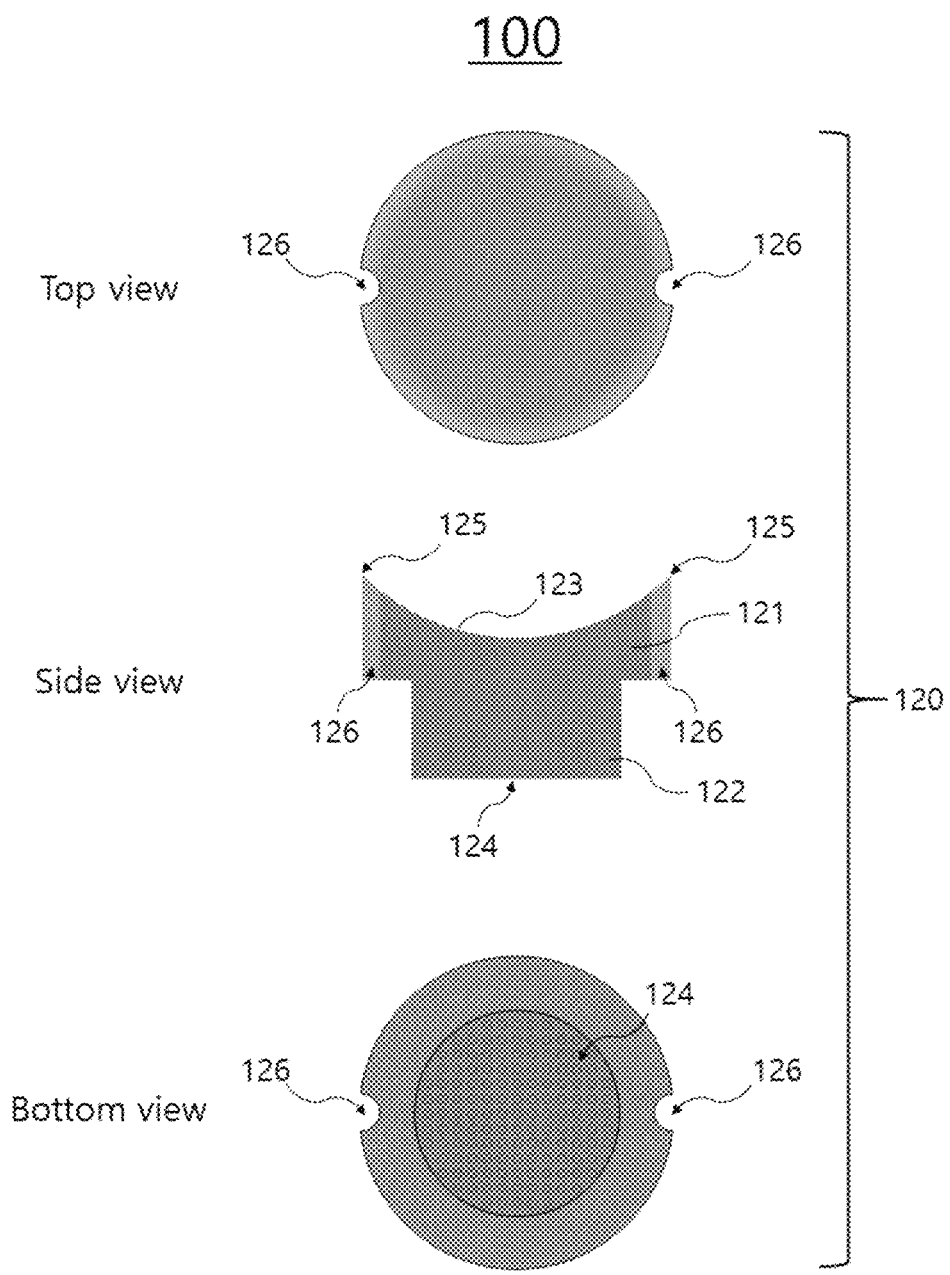
FIG. 4 is a schematic perspective view of one embodiment of a cell isolation device.

Another aspect of the present disclosure provides a cell isolation device for cell morphological analysis. FIG. 4 is a schematic perspective view of one embodiment of the cell isolation device. Referring to FIG. 4, the cell isolation device 100 includes a body 120 made of a swellable material whose volume varies in response to an external stimulus and one or more microwells (not illustrated) patterned at least one side of the body 120. The cell isolation device may have a size small enough to be inserted into a well of a substrate.

The body 120 may include a top portion 121 coming into close contact with the inner sidewall of the well when swollen and a bottom portion 122 having a smaller diameter than the top portion 121 so as to be spaced apart from the inner sidewall. The inner portion of the well is easy to observe through the transparent base of the well. Thus, it is preferable that the microwells are formed on the bottom surface 124 of the bottom portion 122.

The body 120 has a concave top surface 123. However, the shape of the top surface 123 is not particularly limited. A relatively thin outer edge portion 125 exists when the top surface 123 is concave unlike when it is flat or convex. When an external stimulus is applied, the swellable material in the outer edge portion 125 swells and is brought into close contact with the inner wall of the well. At this time, the swellable material swells rapidly and the outer edge portion 125 is rapidly brought into close contact with inner wall of the well when the top surface 123 is concave compared to when it is flat or convex. Due to the concave shape of the top surface, the bottom surface of the bottom portion 122 is strongly pressed against the base of the well in the vertical direction of the well during swelling, with the result that cells can be securely isolated in the microwells.

The shape of the bottom surface 124 of the bottom portion 122 is not particularly limited but is preferably flat as a whole taking into consideration adhesion to the base of the well and ease of patterning the microwells.

In one embodiment, the cell isolation device may further include bubble holes 126 formed on the flank of the top portion 121 to allow air bubbles generated in the space during swelling of the swellable material to escape therethrough.

The swellable material is preferably a hydrogel. The observation of single bacterial cells requires immobilization of the bacterial cells. For example, this immobilization may be accomplished using the microwell-patterned hydrogel structure. The microwell-patterned hydrogel structure has a diameter of 2 to 900 μm, preferably 5 to 100 μm, more preferably 10 to 60 μm. For example, when the microwell-patterned hydrogel structure is inserted into a 96 well plate, the dimensions of the hydrogel structure may be 40 μm in diameter and 5 μm in height. With these dimensions, time-lapse optical images of individual bacterial cells can be effectively analyzed.

Any energy or external substance that can induce a change in the volume of the swellable material when applied to the swellable material may be used without particular limitation as the external stimulus. The external stimulus can be selected from the group consisting of light, sound, heat, electricity, magnetism, specific substances, and combinations thereof. Here, the specific substances may be gaseous, liquid, and solid substances, for example, water, organic solvents, acids, and bases. When the swellable material is a hydrogel, the external stimulus is preferably water. The water may be supplied from a cell culture medium. The time and degree of swelling vary depending on the ratio of water to polymer mixture in the hydrogel. Thus, optimal ratios are determined to be suited to the well plate platform.

As described above, the diameter of the bottom portion 122 of the cell isolation device 100 is smaller than that of the top portion 121, which is preferred for ease of observation. FIG. 5 compares the structures of two cell isolation devices including bottom portions having different diameters. Top and bottom portions of the cell isolation device shown in the left images of FIG. 5 have the same diameter. Top and bottom portions of the cell isolation device shown in the right images of FIG. 5 have different diameters. The two top images are lateral views and the two bottom images are top views.

Referring to FIG. 5, floating bacterial cells in the concave portion of the top surface of the hydrogel structure settle and are more likely to become denser over time than those at the perimeter of the structure. Furthermore, since the curvature of the upper edge portion is very steep, the perimeter may become a critical problem for light propagation necessary for observation. As a result, it may be difficult to observe cells present at the center and the perimeter.

When the hydrogel structure whose top and bottom portions have the same diameter swells and comes into close contact with the inner sidewall of the well, a strong pressure acts on the lower end of the fixation part and a weak pressure acts over substantially the entire area of the hydrogel structure (see the left views). As a result, only the outer perimeter of the swollen hydrogel will be in contact with the base of the well, so the trapped cells will be isolated in this outer area. However, it may be difficult to observe cells at the perimeter for light transmission, as described above.

In contrast, when the hydrogel structure whose top and bottom portions have different diameters swells, an extra space is created at the perimeter, a strong pressure is applied to the area between the center and the perimeter, and a weak pressure is applied only to the center. Therefore, cells can be readily trapped in the ring-shaped area where a strong pressure is applied. In this case, cells can be trapped in the area that avoids the perimeter and the center where light does not readily penetrate, facilitating observation of the morphological changes of the cells. In the lateral views, the areas of disturbing observation and the undisturbed areas to observe cells are indicated by dashed lines.

In order to clearly observe the isolated bacteria, it is preferred to modify the hydrogel structure such that the area that is pressed against the base of the well will form a ring that avoids the perimeter and the center of the well. To this end, the diameter of the bottom portion of the hydrogel structure is reduced to avoid trapping the bacteria at the perimeter, as shown in the right views. The radius of the area of the pressure part may be reduced. In this case, the pressure part applies a stronger pressure to the base of the well than the pressure part of the hydrogel structure whose top and bottom portions have the same diameter.

Another advantage is that since air bubbles generated in the space during swelling of the hydrogel can escape through the extra space, the microwells can be brought into close contact with the base of the well. Air bubbles can be more easily released through the bubble holes formed at the fixation part of the top portion. The bubble holes may take the form of grooves inscribed on the flank of the top portion of the hydrogel.

Figure 6:
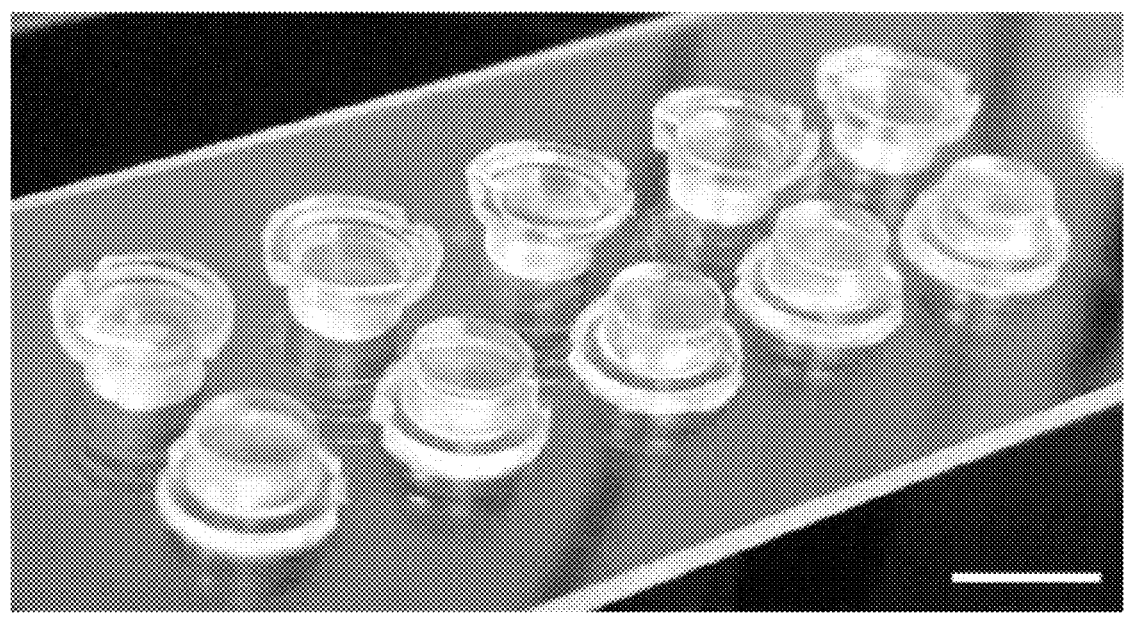
FIG. 6 is a photograph of hydrogel structures fabricated by design optimization through experiments.

FIG. 6 is a photograph of hydrogel structures fabricated by design optimization through experiments. Referring to FIG. 6, the upright and flipped hydrogel structures are arrayed.

Yet another aspect of the present disclosure provides a kit for cell isolation and morphological analysis. The kit includes a substrate with one or more wells and the cell isolation device inserted and arranged in each well of the substrate. The cell isolation device may be arranged such that the microwells at the bottom surface of the bottom portion face the base of the well.

The use of the kit offers increased convenience to a user for cell analysis. For example, a user can purchase the kit in which the hydrogel structures are previously inserted into the wells of the 96 well plate and can simply introduce a sample containing target cells together with appropriate reactants into the wells to induce the desired responses of the cells in a short time.

The kit can be very conveniently used to determine the minimum inhibitory concentrations of antibiotics. After a sample containing cell colonies is mixed with a nutrient medium and different kinds and concentrations of antibiotics are introduced into the wells of the kit, the morphological changes of the cells in response to the antibiotics can be rapidly observed in a state in which the cell colonies are trapped at the level of individual cells.

The present disclosure provides an antibiotic susceptibility test culture system to observe and analyze the growth pattern of single bacterial cells using simple hydrogel bacterial isolation devices in a conventional 96 well plate without extra apparatus and processes. In the system, the simple hydrogel bacterial isolation device is designed to isolate the bacterial cells and expose the bacterial cells to the sufficient space for bacterial culture in a stress-free environment.

The methods for cell isolation and morphological analysis according to the foregoing embodiments possess considerable potential as rapid antibiotic susceptibility testing methods in the clinical arena. Additionally, the methods enable very efficient isolation of diverse types of cells without uncomplicated processes to observe single cell morphology, so they can be adopted widely for general cell research.

The present disclosure will be explained in more detail with reference to the following examples.

EXAMPLES

Example 1: Setup of Optical Maskless Lithography System

An optofluidic maskless lithography (OFML) system was used to fabricate various shapes of microwell patterns. The OFML system consisted of an ultraviolet (UV) light source, a mercury-xenon lamp (200 W bulb, Hamamatsu) with a fiber-based light guide as a continuous light source, to solidify a photocurable polymer and a digital micromirror device (DMD, 1024×768 pixels, Texas Instruments) to generate a micromirror pattern for forming desired UV patterns (microwell patterns). The UV source and DMD were installed with an optical microscope (IX71 Olympus). A charge coupled device (CCD, DP73) camera equipped with the optical microscope and imaged the microwell patterns that were generated.

Example 2: Top and Bottom PDMS Mold Fabrication

In order to fabricate the bottom polydimethylsiloxane (PDMS, Dow Corning) mold, a glass slide substrate (stamp mold) coated with 3-(trimethoxysilyl)propyl methacrylate (TMSPMA, Sigma-Aldrich) was prepared to enhance bonding between the glass surface and the photocurable polymer patterns before creating the microwell patterns. First, a 2% 3-(trimethoxysilyl) propyl methacrylate was diluted in ethanol (99%, DAEJUNG) and mixed evenly. After mixing, the solution was sprayed on the glass substrate and dried at room temperature for 10 minutes. Finally, the dried glass slide substrate was baked at 100° C. on a hot plate for one minute.

For the top polydimethylsiloxane (PDMS, Dow Corning) mold, a three-dimensional printer (Form 1+, Formlabs) printed a stamp mold with the desired design. After preparing the stamp molds, the PDMS material poured onto the stamp molds and baked at 65° C. on a hot plate overnight.

Example 3: Polymer Materials

UV-curable photoresin, polyurethane acrylate (PUA311, Minuta Tech), was adopted to fabricate the microwell-patterned substrate. Poly(ethylene glycol) diacrylate (PEGDA, Sigma-Aldrich, Mn=700) with 10% v/v of photoinitiator (2-Hydroxy-2-methylpropiophenone, Irgacure 1173, Sigma-Aldrich) was used as the photocurable hydrogel solution.

Example 4: Measurement of the Degree of Swelling of the Hydrogel Mixture

First, a PDMS mold with a diameter of 6 mm and a height of 1.12 mm was prepared to form the prepolymer hydrogels. After fabricating the mold, the photocurable hydrogel solution of poly(ethylene glycol) diacrylate (PEGDA, Sigma-Aldrich, Mn=700) was mixed with distilled water according to the desired ratios (PEGDA to water, 1:0, 1:1, 1:3, 1:7 (v/v)). This mixture was poured into the PDMS mold, cured for 1 minute in a UV chamber, and dried overnight. The external appearance of the hydrogel structure, concavity, flatness, and convexity, varies depending on the amount of prepolymer poured into the remaining space of the assembled PDMS molds. The concave microwell-patterned hydrogel structure was used in this example.

The wet swelling rates of the fabricated microwell-patterned hydrogel structure were analyzed. As a result, the dried structural size became smaller as the ratio of distilled water in the mixture of the polymer material and distilled water increased and the hydrogel structure swelled rapidly in a short time. From the results, the size and swelling rate of the hydrogel structure were found to be optimal when the ratio of PEGDA to distilled water was 1:1 (v/v).

The diameter, 7.4 mm, and depth, 3.27 mm, of the top PDMS mold were designed to fit the well size of a conventional 96 well plate.

Example 5: Bacterial Cell Culture

For the Saccharomyces cerevisiae (yeast) cultures, the final inoculum concentration of each well was set to $3 \times 10^8$ CFU/mL with Yeast-Malt broth (YM broth, Sparks, MD) and growth was observed at 30° C. In the case of the Streptomyces atratus (spore-type actinomycetes) cultures, the final cell concentration of the wells was controlled at $7.5 \times 10^7$ CFU/mL with tryptic soy broth (TSB, Sparks, MD) and growth was at 28° C. For the E. coli ATCC 25922, Staphylococcus aureus ATCC 29213, and methicillin resistant Staphylococcus aureus cultures, the initial concentration of bacterial cells injected into each well was set to $3 \times 10^8$ CFU/mL with Mueller-Hinton broth (MHB, Fluka Analytical). In order to adjust the concentration of antibiotics, ampicillin (Sigma-Aldrich) and chloramphenicol (Sigma-Aldrich), a two-fold serial dilution method was used. After that, 227.5 μL (91% v/v) of Mueller-Hinton broth (MHB, Fluka Analytical), 2.5 μL (1% v/v) of the antibiotics, and 20 μL (8% v/v) of bacterial cells were mixed and growth was monitored at 37° C.

Figure 7:
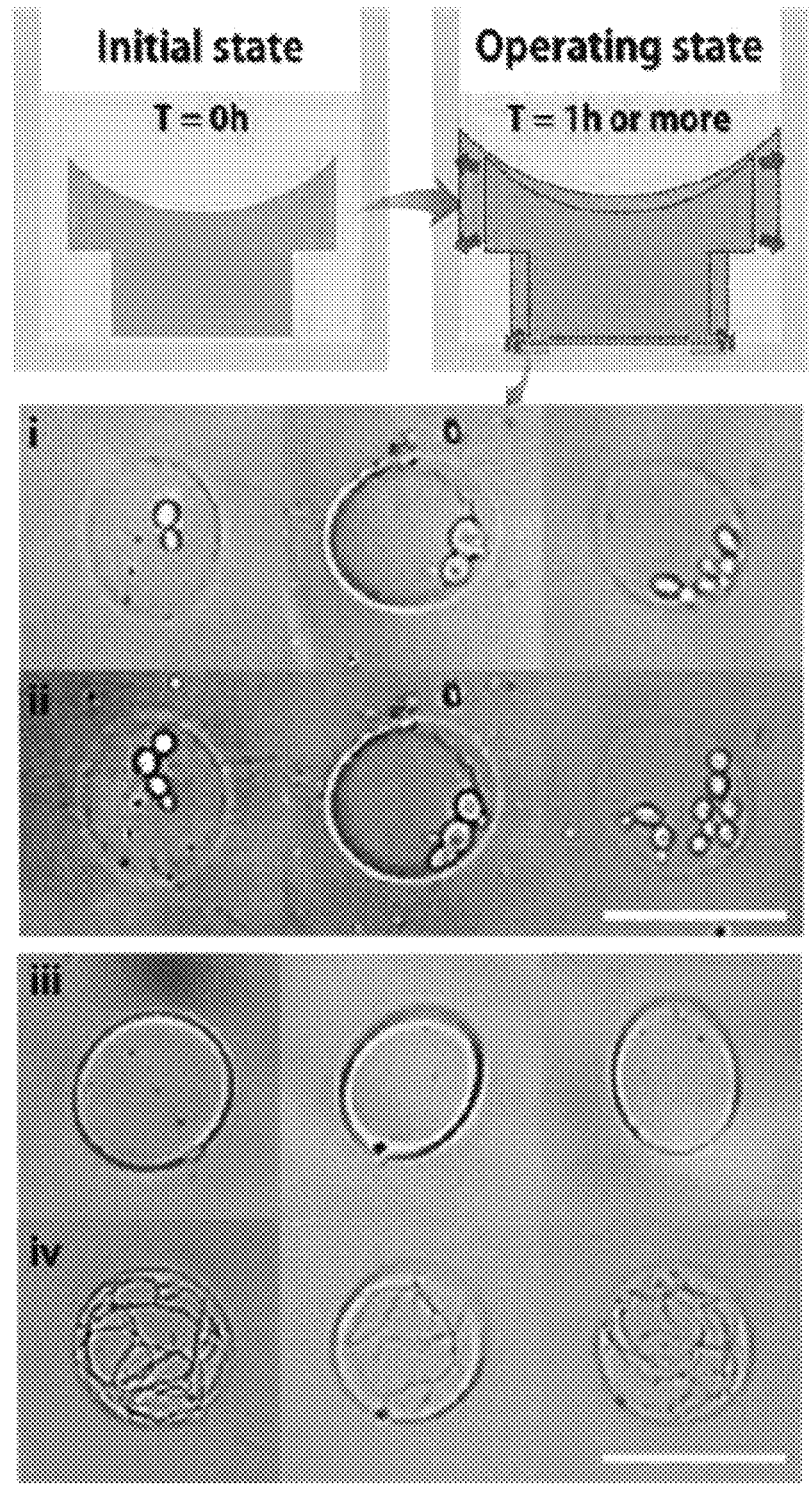
FIG. 7 shows the growth of yeast cells in hydrogel structures according to one embodiment of the present disclosure inserted into 96 well plates, which was observed under a microscope.

Example 6: Optimization of the Hydrogel Swelling and Imaging the Growth of Individual Cells Under the Hydrogel Bacterial Isolation Device FIG. 7 shows the growth of yeast cells in the hydrogel structures according to one embodiment of the present disclosure inserted into 96 well plates, which was observed under a microscope. The top left view shows the initial state after insertion of the hydrogel structure and the top right view shows the operating state after 1 h or more. i, ii, iii and iv of FIG. 7 are microscopy images of the bacterial cells isolated in the microwells, which were observed through the bottom surfaces of the bottom portions of the hydrogel structures.

Referring to FIG. 7, to show different types of single cell growth, two types of bacterial cells (*S. cerevisiae* (yeasts), germination growth) and *S. atratus* (actinomycetes), filamentary growth) were observed in conventional 96 well plates using the generated microwell-patterned hydrogel. After introduction of these cells, nutrients, and antibiotics, the first cell growth images (i and iii of FIG. 7) were photographed after 1 hour, allowing sufficient time to inflate the microwell-patterned hydrogel to fit tightly into each well, and the second images (ii and iv of FIG. 7) were captured after two hours or after one day depending on the growth rate of the bacteria.

In the case of the yeast cells, within one hour several cells were isolated from cell colonies inserted into each well (i of FIG. 7), and the trapped cells inside the microwells of the hydrogel structure were observed after another hour to verify the bacterial growth. Thus, two hours after starting the experiment, the yeast cells were examined, and the cell differentiation process, budding, was observed in all of independent microcells tested (ii of FIG. 7).

In the case of actinomycetes, the bacterial cells are difficult to isolate individually because the actinomycetes grow in a filamentary form and the cell sizes are not uniform. Therefore, a spore type actinomycetes with appropriate size, 0.5-1 μm diameter, was adopted to allow the cells to enter individually into the microwells of the microwell-patterned hydrogel.

As with the yeast, the first cell growth images were photographed after one hour (iii of FIG. 7) and after one day. The second growth images were captured after one full day because this type of cell requires a relatively long time to undergo several cell divisions. The actinomycetes showed sufficient growth to fill the microwell (iv of FIG. 7).

These results demonstrate that various cell types including different cell morphologies and growth rates can be tested with this rapid antibiotic susceptibility testing system.

Example 7: Determination of Minimum Inhibitory Concentration (MIC) Values of Antibiotics for Rapid Antibiotic Susceptibility Test In this example, the Clinical Laboratory Standard Institute (CLSI) standard strains, *Escherichia coli* (*E. coli*) ATCC 25922 and *Staphylococcus aureus* (*S. aureus*) ATCC 29213 were tested with various concentrations of ampicillin and chloramphenicol to determine the minimum inhibitory concentration (MIC) values of the antibiotics. The rapid antibiotic susceptibility test results were compared with the previous antibiotic susceptibility test results. The cell growth images were recorded every hour for four hours to observe the change in cell number and morphological change to indicate growth.

The *E. coli* cell's morphological reaction to various ampicillin concentrations was analyzed.

Figure 8:
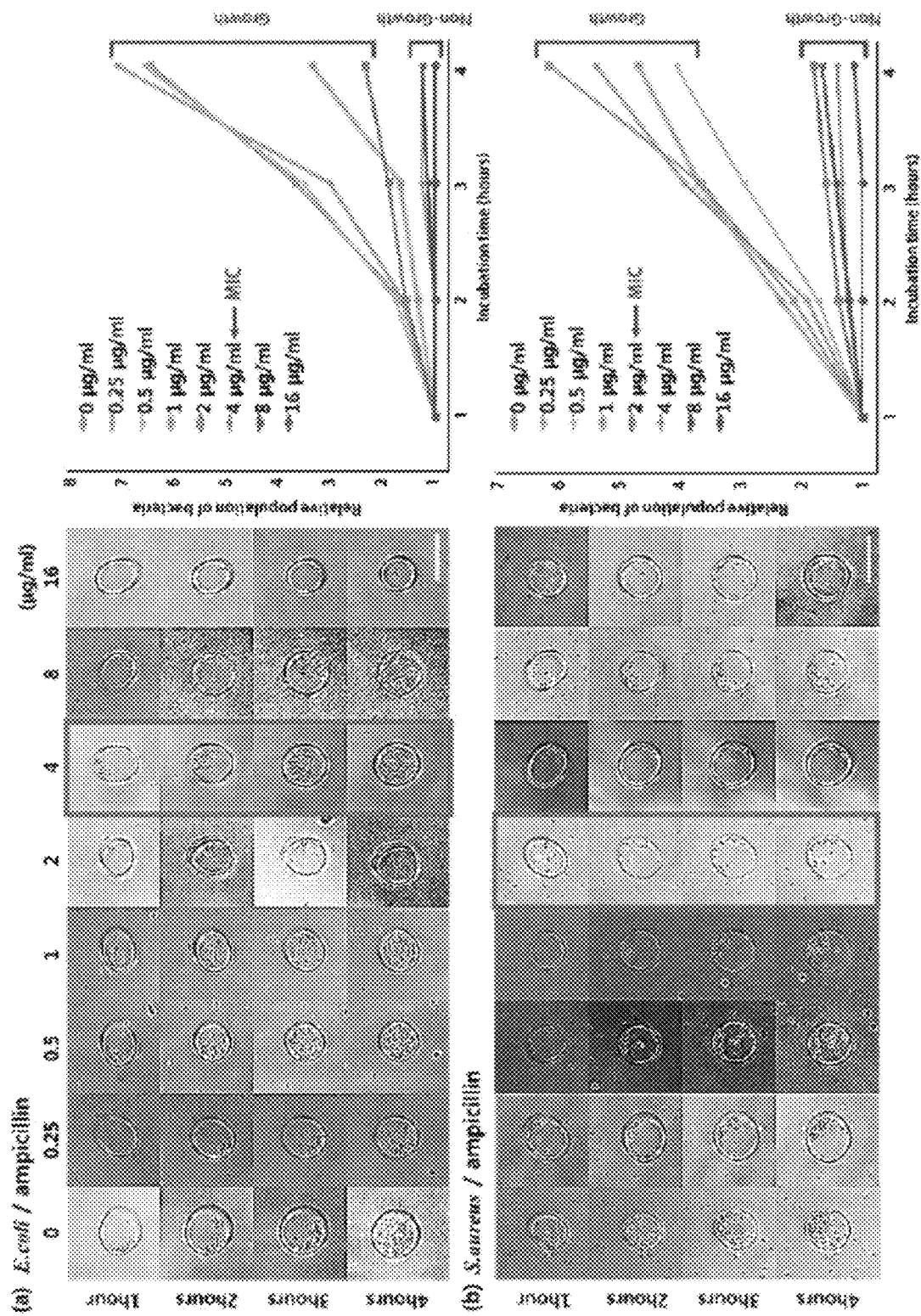
FIG. 8 shows MIC determination for *Escherichia coli* and *Staphylococcus aureus* strains by analyzing bacterial size and number under different concentrations of ampicillin.

FIG. 8 shows MIC determination for the *Escherichia coli* and *Staphylococcus aureus* strains by analyzing bacterial size and number under different concentrations of ampicillin. Referring to (a) of FIG. 8, the *E. coli* cells could not divide with concentrations of 2 μg/mL or more ampicillin concentration and showed filamentary growth. However, the cells could divide concentrations under 2 μg/mL. These results are consistent with the previous antibiotic susceptibility test results. Referring to (b) of FIG. 8, in the morphological reaction of the *S. aureus* cells to various ampicillin concentrations, when the concentration of ampicillin was 2 μg/mL or more, the bacterial cells could not divide or grow. From these optical microscopic images, the minimum inhibitory concentration (MIC) values of *E. coli* and *S. aureus* against ampicillin antibiotics were determined to be 4 μg/mL and 2 μg/mL, respectively, and the minimum inhibitory concentration (MIC) results satisfied the CLSI minimum inhibitory concentration (MIC) ranges (2-8 μg/mL of *E. coli* ATCC 25922 and 0.5-2 μg/mL of *S. aureus* ATCC 29213).

Figure 9:
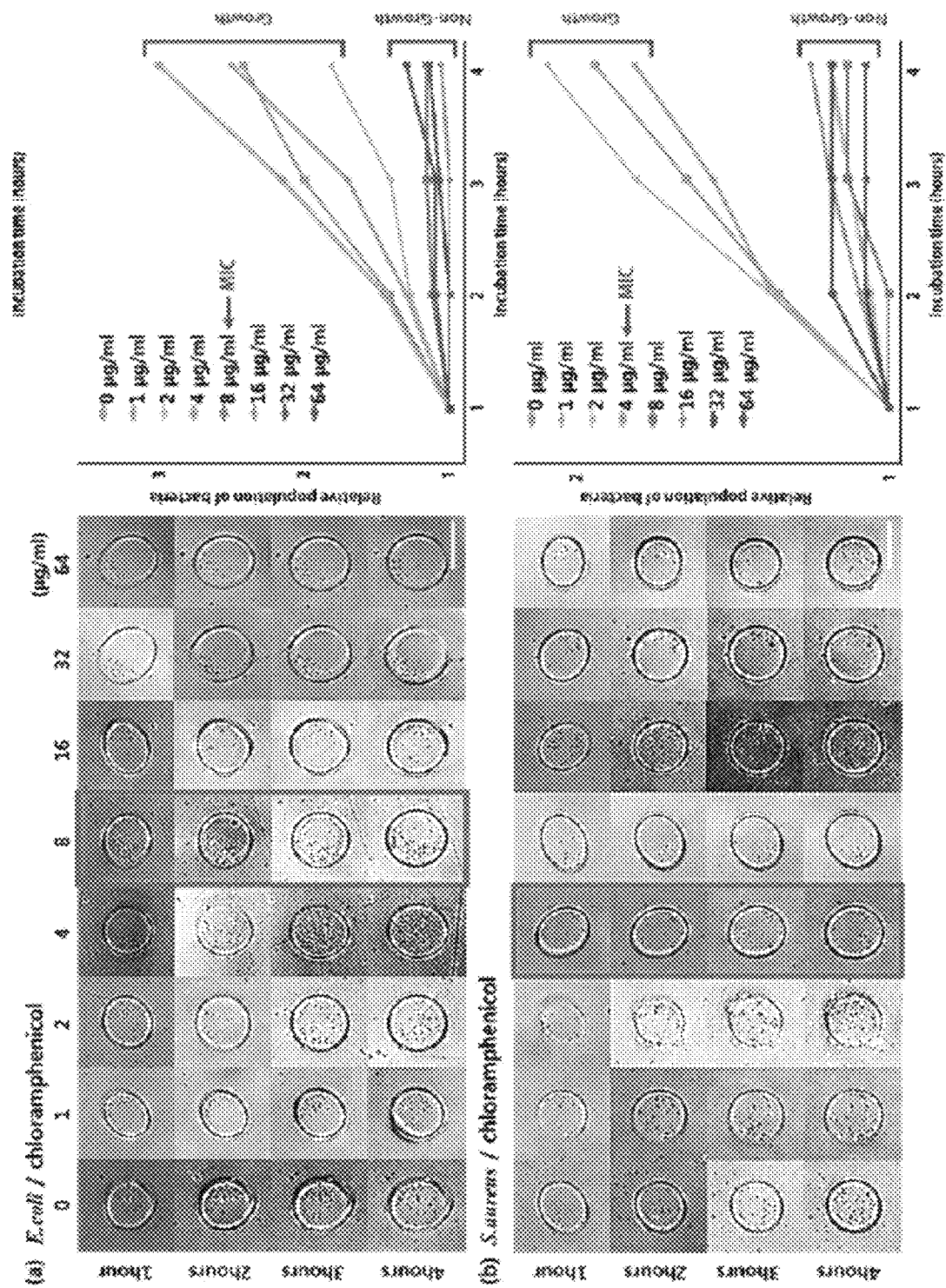
FIG. 9 shows MIC determination for *Escherichia coli* and *Staphylococcus aureus* strains by analyzing bacterial size and number under different concentrations of chloramphenicol.

FIG. 9 shows MIC determination for the *Escherichia coli* and *Staphylococcus aureus* strains by analyzing bacterial size and number under different concentrations of chloramphenicol. The minimum inhibitory concentration (MIC) values of *E. coli* ATCC 25922 and *S. aureus* ATCC 29213 against chloramphenicol antibiotics were 8 μg/mL ((a) of FIG. 9) and 4 μg/mL ((b) of FIG. 9), respectively, which were consistent with the CLSI minimum inhibitory concentration (MIC) ranges (2-8 μg/mL of *E. coli* ATCC 25922 and *S. aureus* ATCC 29213).

Figure 10:
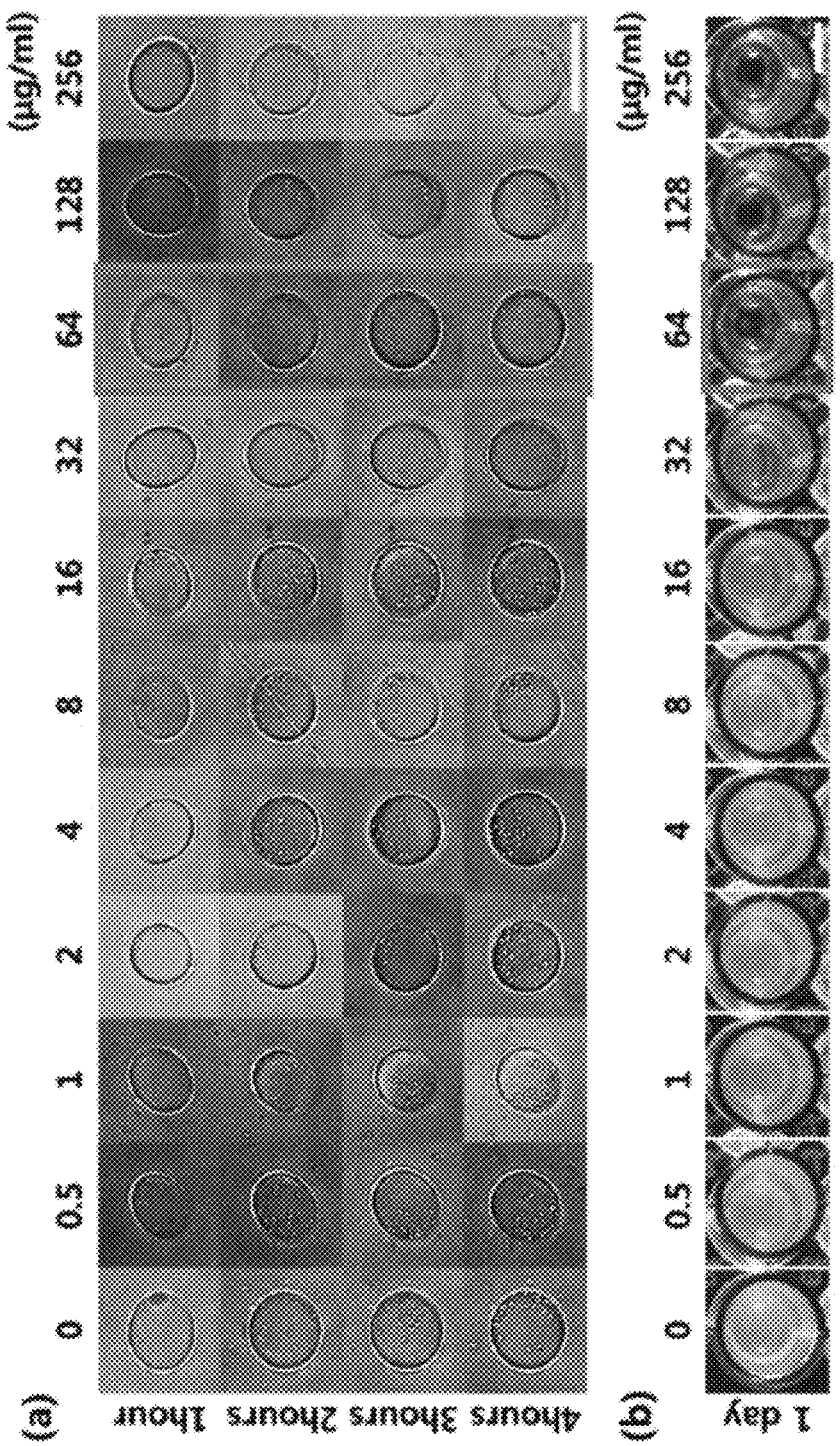
FIG. 10 shows minimum inhibitory concentration (MIC) determination of methicillin-resistant *Staphylococcus aureus* (MRSA) with different concentrations of ampicillin.

The minimum inhibitory concentration (MIC) values of methicillin-resistant *Staphylococcus aureus* (MRSA) against ampicillin antibiotics are shown in (a) and (b) of FIG. 10.

FIG. 10 shows minimum inhibitory concentration (MIC) determination of methicillin-resistant *Staphylococcus aureus* (MRSA) with different concentrations of ampicillin. (a) of FIG. 10 shows minimum inhibitory concentration (MIC) results of ampicillin antibiotics measured by the rapid antibiotic susceptibility test method whose running time is 4 hours using the microwell-patterned hydrogel structures according to one embodiment of the present disclosure. (b) of FIG. 10 shows minimum inhibitory concentration (MIC) results of ampicillin antibiotics measured by the conventional antibiotic susceptibility test method whose running time is 18-24 hours using turbidity. As a result, both antibiotic susceptibility test methods showed the same minimum inhibitory concentration (MIC) value of ampicillin antibiotics (64 μg/mL).

As is apparent from the foregoing, the MIC results using the hydrogel bacterial isolation device according to one embodiment of the present disclosure were in agreement with those of the CLSI MIC ranges.

Although the present disclosure has been described in detail with reference to the drawings and embodiments, those skilled in the art will appreciate that various variations and modifications can be made to the embodiments without departing from the spirit of the present disclosure as set forth in the appended claims.

What is claimed is:

1. A cell isolation device for cell analysis comprising:
a body (120),
wherein,
the body (120) comprises a top portion (121) and a bottom portion (122), wherein the top portion (121) comprises a top surface (123) and an outer edge portion (125) and the bottom portion (122) has a bottom surface (124),
the body (120) is made of a swellable material,
bubble holes (126) are formed on a flank of the top portion (121),
one or more microwells are patterned at least on the bottom surface (124), and the bottom portion and the top portion have a cylindrical shape, and the bottom portion (122) has a smaller diameter than the top portion (121).

2. The cell isolation device according to claim 1, wherein the swellable material is capable of being swollen by an external stimulus, wherein the external stimulus is selected from the group consisting of electricity, light, sound, heat, magnetism, specific substances, and combinations thereof.

3. The cell isolation device according to claim 1, wherein the swellable material is a hydrogel.

4. The cell isolation device according to claim 1, wherein the top surface (123) is concave.

5. A kit for cell isolation and morphological analysis comprising a substrate having one or more wells and a plurality of the cell isolation devices and each of the plurality of the cell isolation devices is according to claim 1 and is inserted and arranged in each well of the substrate.

* * * * *